United States Patent [19]

Le et al.

[11] Patent Number: 5,107,049
[45] Date of Patent: * Apr. 21, 1992

[54] STABILIZATION OF POLYALPHA-OLEFINS

[75] Inventors: Quang N. Le, Cherry Hill; Joosup Shim, Wenonah; Stephen S. Wong, Medford, all of N.J.

[73] Assignee: Mobil Oil Corporation, Fairfax, Va.

[*] Notice: The portion of the term of this patent subsequent to May 28, 2008 has been disclaimed.

[21] Appl. No.: 593,171

[22] Filed: Oct. 5, 1990

Related U.S. Application Data

[63] Continuation-in-part of Ser. No. 515,030, Apr. 26, 1990, Pat. No. 5,019,670, which is a continuation-in-part of Ser. No. 469,999, Jan. 25, 1990, Pat. No. 4,962,256, which is a continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............................................. C07C 2/66
[52] U.S. Cl. .................................... 585/467; 585/24; 585/26
[58] Field of Search ................... 585/24, 26, 446, 467

[56] References Cited

U.S. PATENT DOCUMENTS

| | | | |
|---|---|---|---|
| 2,904,607 | 9/1959 | Mattox et al. | 585/467 |
| 3,251,897 | 5/1966 | Wise | 585/467 |
| 3,751,504 | 8/1973 | Keown et al. | 585/467 |
| 3,751,506 | 8/1973 | Burress | 585/446 |
| 4,211,665 | 7/1980 | Pellegrini, Jr. | 585/24 |
| 4,238,343 | 12/1980 | Pellegrini, Jr. | 585/24 |
| 4,439,409 | 3/1984 | Puppe et al. | 423/328 |
| 4,604,491 | 8/1986 | Dressler et al. | 585/26 |
| 4,714,794 | 12/1987 | Yoshida et al. | 585/467 |
| 4,826,667 | 5/1989 | Zones et al. | 423/277 |
| 4,954,325 | 9/1990 | Rubin et al. | 502/74 |
| 4,962,256 | 10/1990 | Le et al. | 585/446 |
| 4,990,718 | 2/1991 | Pelrine | 585/467 |
| 5,001,295 | 3/1991 | Angevine et al. | 585/467 |
| 5,019,670 | 5/1991 | Le et al. | 585/467 |

FOREIGN PATENT DOCUMENTS 0293032 5/1988 European Pat. Off. .
2078776 6/1981 United Kingdom .

*Primary Examiner*—Anthony McFarlane
*Attorney, Agent, or Firm*—Alexander J. McKillop; Charles J. Speciale; Malcolm D. Keen

[57] ABSTRACT

The thermal stability of poly alpha-olefin (PAO) lubricant basestocks are improved by reacting an aromatic compound with the alpha-olefin oligomer. The PAO materials are prepared by oligomerization of olefins such as 1-decene in the presence of a Lewis acid oligomerization catalyst. The resulting lubricant basestock product exhibits high viscosity, viscosity index and low pour point in addition to the unique enhancement in thermal stability. The reaction between the PAO and the aromatic is carried out in the presence of a solid, cyrstalline alkylation catalyst identified by a specific X-ray diffraction pattern. The preferred catalyst for this purpose is the material known as MCM-22.

15 Claims, No Drawings

STABILIZATION OF POLYALPHA-OLEFINS

CROSS-REFERENCE TO RELATED APPLICATIONS

This application is a continuation-in-part of prior application Ser. No. 07/515,030, filed 26 Apr. 1990, of Q. N. Le et al. now U.S. Pat. No. 5,019,670.

Ser. No. 07/515,030, in turn, is a continuation-in-part of application Ser. No. 07/469,999, filed 25 Jan. 1990, of Q. N. Le et al., which was a continuation-in-part of Ser. No. 07/254,524, filed 6 Oct. 1988, now U.S. Pat. No. 4,954,325. Ser. No. 07/254,524 was a continuation-in-part of Ser. No. 06/98,176, filed 18 Sep. 1987, now abandoned, which, in turn, was a continuation-in-part of Ser. No. 06/890,268, filed 29 Jul. 1986, now abandoned.

FIELD OF THE INVENTION

This invention relates to a process for the stabilization of polyalpha-olefin (PAO) liquid lubricants. More particularly, the invention relates to a process for reacting unsaturated PAO oligomers with aromatic compounds to provide liquid lubricants that exhibit improved thermal stability and oxidative stability compared to the stability of the PAO oligomer starting material. These improvements are achieved without impairing the superior lubricant properties of the preformed PAO.

BACKGROUND OF THE INVENTION

Efforts to improve upon the performance of natural mineral oil based lubricants by the synthesis of oligomeric hydrocarbon fluids have been the subject of important research and development in the petroleum industry for at least fifty years and have led to the relatively recent market introduction of a number of superior polyalpha-olefin (PAO) synthetic lubricants, primarily based on the oligomerization of alpha-olefins or 1-alkenes. In terms of lubricant property improvement, the thrust of the industrial research effort on synthetic lubricants has been toward fluids exhibiting satisfactory viscosities over a wider range of temperatures, i.e.,improved viscosity index (VI), while also showing lubricity, thermal and oxidative stability and pour point equal to or better than mineral oil. These new synthetic lubricants may also be capable of decreasing friction and, by so doing, increasing mechanical efficiency of mechanical devices, especially where there is any significant sliding or rolling contact, for example, worm gears, other gear forms and traction drives, and do this over a wider range of operating conditions than mineral oil lubricants.

Notwithstanding their generally superior properties, PAO lubricants are often formulated with additives to enhance those properties for specific applications. The more commonly used additives include oxidation inhibitors, rust inhibitors, metal passivators, antiwear agents, extreme pressure additives, pour point depressants, detergent-dispersants, viscosity index (VI) improvers, foam inhibitors and the like, as described, for example, in Kirk-Othmer "Encyclopedia of Chemical Technology", 3rd edition, Vol. 14, pp477-526. Improvements in lubricant technology have come from new additive development addressed to deficiencies in lubricant oligomers and new base fluid development for inherently better properties.

Alkylated aromatics, particularly alkylated naphthalene, are known in the prior art as lubricant additives for their thermal and oxidative stability as disclosed in U.S. Pat. Nos. 4,211,665, 4,238,343, 4,604,491 and 4,714,7944. GB 2 078 776 discloses the preparation of alkylaromatic compounds by the reaction of olefin polymers with benzene or lower alkyl benzenes and describes their use as lubricating fluids of high viscosity, high VI and low pour point. The antiwear properties of alkylnaphthalene compounds are presented in Khimiya i Tekhnologiya Topliv i Masel, No. 8, pp. 28-29, August, 1986; these materials are thought to show promise as base stocks for lubricants.

The preparation of PAO lubricants is conventionally carried out by the catalytic oligomerization of linear alpha-olefins having between six and twenty carbon atoms employing a Lewis acid or Ziegler catalyst to form olefinic oligomers which are usually are hydrogenated to stabilize them before their formulation with additives and application as lubricants. Examples of alpha-olefin oligomerization are described in the publication by Brennan, Ind. Eng. Chem. Prod. Res. Dev. 1980, 19, 2-6. For high viscosity synthetic hydrocarbon lubricants from alpha-olefins aluminum chloride ($AlCl_3$) is a preferred catalyst as described in U.S. Pat. Nos. 3,725,498, 3,833,678 and 4,239,927, to which reference is made for a description of the methods by which these materials may be made. These products show high viscosity index (VI) and low pour point. PAO is also prepared with promoted $BF_3$ catalyst to produce a lower molecular weight oligomer containing residual olefinic unsaturation in the as oligomerized conditions.

SUMMARY OF THE INVENTION

We have now found that the thermal stability of PAO lubricant basestock can be substantially improved by reacting an aromatic compound with the pre-formed alpha-olefin oligomer. The reaction between the aromatic compound and the olefin oligomer is carried out in the presence of an alkylation catalyst of a particular type, as described below. The olefinic oligomer is normally prepared by the oligomerization of suitable olefins in the presence of a Lewis acid oligomerization catalyst. The resulting lubricant basestock product exhibits high viscosity, viscosity index and low pour point in addition to the unique enhancement in thermal stability.

In the process, a mixture comprising a major portion of preformed $C_6$-$C_{20}$ alpha-olefin oligomer and a minor portion of aromatic compound are reacted with one another in the presence of a solid, crystalline alkylation catalyst in the presence of a solid, crystalline alkylation catalyst acidic catalyst under alkylation conditions to produce the liquid lubricant basestock of improved thermal stability.

According to the present invention, the oligomer is reacted with the aromatic compound in the presence of a solid, crystalline alkylation catalyst which comprises a solid, porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

A preferred catalyst of this type includes the synthetic zeolite identified in this specification as MCM-22.

The alkylated products have been found to possess good thermal and oxidative stability as well as good additive solvency characteristics in addition to their characteristically excellent fluid flow properties attributable to the olefin oligomers.

DETAILED DESCRIPTION OF THE INVENTION

Olefin Oligomers

In the present process aromatic compounds are alkylated with olefinic PAO oligomers using a particular type of solid, crystalline acidic catalyst. The PAO oligomers may be prepared by conventional methods, including especially the Lewis acid catalyzed oligomerization of alpha-olefins. $AlCl_3$, $BF_3$ and complexes of $BF_3$, especially complexes with alcohols and esters, are suitable catalysts which are preferred to prepare the unsaturated PAO materials used in the present invention as starting material. The alpha-olefins used to prepare the PAO include those olefins containing from 6 to about 20 carbon atoms such as 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha-olefinic as for example 1-hexene to 1-hexadecene and more preferably 1-octene to 1-tetradecene, especially 1-decene, or mixtures of such olefins.

The PAO oligomers used as starting material in the present invention are preferably olefinic $C_{30}$-$C_{5000}$ liquid hydrocarbon oligomers having a branch ratio greater than 0.19. Oligomers in the $C_{30}$-$C_{50}$ molecular weight range are preferred. Branch ratio refers to the ratio of $CH_3/CH_2$ in the oligomer as determined by I. R. analysis. The ratio is called the branch ratio and is calculated from infra red data as discussed in "Standard Hydrocarbons of High Molecular Weight", *Analytical Chemistry*, Vol.25, no.10, p.1466 (1953). Pour points (ASTM U-97 or equivalent, e.g. Autopour) of less than −15° C. are preferred for the oligomers.

Aromatic Compound

The aromatic compounds which may be used as coreactant with the PAO oligomers in the alkylation reaction include substituted or unsubstituted mono or polynuclear aromatic compounds containing six to twenty carbon atoms. These aromatic compounds include benzene, naphthalene, phenanthrene, toluene, o,m,p-xylene, hemimellitene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenylmethane, 1,2-diphenylethane and similarly alkyl or aryl substituted naphthalene, phenanthrene and anthracene; also phenol, catechol, anisole, chlorobenzene, diphenylcarbonate, aniline, acetanilide, ethylbenzoate, thiophenol, alkylphenylsulfide, nitrobenzene, diphenylether, diphenylsulfide, 1-hydroxy and 2-hydroxy naphthalene and similarly substituted anthracene and phenanthrene.

Alkylation Catalyst

The catalyst which is used in the alkylation reaction is a solid, porous acidic catalytic material which a characteristic X-ray diffraction pattern. In its calcined form, the synthetic porous crystalline material component employed in the catalyst is characterized by an X-ray diffraction pattern including the lines shown in Table 1 below:

TABLE 1

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |

TABLE 1-continued

| Interplanar d-Spacing (A) | Relative Intensity, $I/I_o \times 100$ |
|---|---|
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines shown in Table 2 below:

TABLE 2

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines shown in Table 3 below:

TABLE 3

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines shown in Table 4 below:

TABLE 4

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |

TABLE 4-continued

| Interplanar d-Spacing (A) | Relative Intensity, $I/I_o \times 100$ |
|---|---|
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1-4, the relative intensities are given in terms of the symbols W = weak, M = medium, S = strong, VS = very strong. In terms of intensities, these may be generally designated as follows:

W = 0-20
M = 20-40
S = 40-60
VS = 60-100

These X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, to which reference is made for a description of this material as well as of its preparation. Another crystalline material of this type is the synthetic zeolite MCM-22. The preferred catalyst is zeolite MCM-22 is capable of producing a reaction product having a viscosity at 100° C. greater than 2cS, a viscosity index greater than 120 and pour point below −15° C.

Zeolite MCM-22 has a chemical composition expressed by the molar relationship:

$$X_2O_3:(n)YO_2.$$

where X is a trivalent element, s aluminum, boron, iron and/or gallium, preferably aluminum, Y is a tetravalent element such as silicon and/or germanium, preferably silicon, and is at least about 10, usually from about to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

where R is an organic component. The Na and R components are associated with the zeolite as a result of their presence during crystallization, and are easily removed by the post-crystalliztion methods described below.

Zeolite MCM-22 is thermally stable a-d exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced at least in part by established techniques including ion exchange with other cations. Preferred replacement cations include metal ions, hydrogen ions, hydrogen precursor ions, e.g., ammonium and mixtures of such ions.

In its calcined form, zeolite MCM-22 appears to be made up of a single crystal phase with little or no detectable impurity crystal phases and has an X-ray diffraction pattern including the lines listed in above Tables 1-4.

Prior to its use as alkylation catalyst, the zeolite crystals should be subjected to thermal treatment to remove part or all of any organic constituent present in the as-synthesised material.

The zeolite in its as-synthesised form containing organic cations as well as when it is in its ammonium form, can be converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to a limit imposed by the irreversible thermal degradation of the crystalline structure of the zeolite, typically up to about 925° C.

Prior to its use in the alkylation process, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, described below, and water. The reaction mixture has a composition, in terms of mole ratios of oxides, within the following ranges:

| Reactants | Useful | Preferred |
| --- | --- | --- |
| YO$_2$/X$_2$O$_3$ | 10–60 | 10–40 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

The organic directing agent for use in synthesizing zeolite MCM-22 from the above reaction mixture is hexamethyleneimine.

In a preferred method of synthesizing zeolite MCM-22, the YO$_2$ reactant contains a substantial amount of solid YO2, e.g., at least about 30 wt.% solid YO$_2$. Where YO$_2$ is silica, the use of a silica source containing at least about 30 wt.% solid silica, e.g., Ultrasil (a precipitated, spray dried silica containing about 90 wt.% silica) or HiSil (a precipitated hydrated SiO2 containing about 87 wt.% silica, about 6 wt.% free H20 and about 4.5 wt.% bound H$_2$O of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days, after which the crystals are separated from the liquid and recovered.

The reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The preparation of various MCM-22 catalytic materials is described in detail in U.S. Pat. No. 4,954,325 (4 Sep. 1990), to which reference is made for a description of this zeolite, its preparation and properties.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material may be composited with another material which is resistant to the temperatures and other conditions employed in the alkylation process of this invention. Such materials include active and inactive materials and synthetic or naturally occurring zeolites as well as inorganic materials such as clays and/or oxides such as alumina, silic or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction. These materials may be incorporated into naturally occurring clays, e.g., bentonite and kaolin, to improve the crush strength of the catalyst under commercial alkylation operating conditions and function as binders or matrices for the catalyst. The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst used in the present process may be increased by steaming. U.S. Pat. Nos. 4,663,492; 4,594,146; 4,522,929; and 4,429,176, describe conditions for the steam stabilization of zeolite catalysts which can be utilized to steam-stabilize the catalyst. Reference is made to these patents for a detailed description of the steam stabilization technique for use with the present catalysys. The steam stabilization conditions typically include contacting the catalyst with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. The steaming of the catalyst can take place under conditions sufficient to initially increase the Alpha Value of the catalyst, the significance of which is discussed below, and produce a steamed catalyst having an enhanced Alpha Value. If desired, steaming can be continued to subsequently reduce the Alpha Value from the higher Alpha Value to an Alpha Value which is substantially the same as the Alpha Value of the unsteamed catalyst.

The Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant =0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), to which reference is made for that description. The experimental conditions of the test reported here include a constant temperature of 538° C. and a variable flow rate as described in detail in the *Journal of Catalysis*. Vol. 61, p. 395.

Alkylation

The alkylation of the aromatic compound with the olefin oligomer is suitably effected by contact of the reactants at a temperature of between about 0° C. and about 500° C., and preferably between about 50° C. and about 250° C. The reaction generally takes place at pressures of from about 0.2 to about 250 atmospheres and preferably from about 1 to about 25 atmospheres. The molar ratio of alkylatable aromatic compound to olefin oligomer alkylating agent can typically be from about 0.1:1 to about 50:1, and preferably can be from about 5:1 to about 5:1. Reaction is suitably accomplished utilizing a feed (oligomer) weight hourly space velocity (WHSV) of between about 0.1 hr$^{-1}$ and about 100 hr$^{-1}$ and preferably from 0.5 hr to about 10 hr$^{-1}$ in a fixed-bed type reaction In a batch type slurry reactor, a continuous stirred tank reactor or in a fixed bed, continuous-flow reactor, the concentration of catalyst in the reaction mixture may be between about 0.1 and 20 weight percent, but preferably about 1 to 5 weight percent, based on the oligomer.

Following alkylation of the PAO, the product may be hydrogenated by conventional means, such as with hydrogen using nickel on a support such as alumina, silica, silkca-alumina or kieselguhr, to produce a lube product having improved thermal and oxidative stability.

EXAMPLE 1

A mixture of 1-decene PAO oligomers obtained from the BF3-propanol promoted Calalyst System was used for the study. The reaction with the selected aromatic (benzene) was carried out in a 1 liter autoclave using about 76 wt % of 1-decene oligomers and 24 wt% of benzene over an acidic MCM-22 zeolite catalyst at 400 psig $N_2$, 205° C. (400° F.) for 6 hours. After the reaction was completed, the MCM-22 catalyst was decanted and the lube fraction distilled to obtain about 88 wt% yield of benzene-containing PAO lube base stock.

Another batch of the decene oligomer was hydrogenated over a Ni-containing catalyst to remove the olefins. Bench-scale product quality testings are performed with these two synthetic lube base stocks and results compared in Table 1, together with the results of the original unhydrogenated starting material. Table 1 indicates that by reacting the PAO with aromatic containing component, both thermal and oxidative stabilities are significantly improved and the results are better than that obtained from hydrogenation over metal containing catalysts.

TABLE 1

| Alkltn. Cat. | Unhydrogenated PAO — | Alkylated PAO MCM-22 | Hydrogenated PAO — |
|---|---|---|---|
| Lube Properties | | | |
| Pour Point, °F. | <−65 | <−65 | <−65 |
| KV @ 40° C., cS | 25.73 | 33.03 | 28.80 |
| KV @ 100° C., cS | 5.23 | 6.04 | 6.70 |
| Viscosity Index | 138 | 131 | 134 |
| Product Quality | | | |
| Thermal Stability @ (550°F.) % Visc. Decrease | 16.4 | 4.6 | 9.1 |
| B-10 Oxidation @ (260° C.), 40 hrs., % Visc. Increase | 120 | 81 | 90 |

EXAMPLE 2

In this example, the decene oligomers were reacted with naphthalene instead of benzene as in Example 1. Table 2 shows that reaction of naphthalene with the unhydrogenated PAO is more effective for improving the oxidation stability than benzene.

TABLE 2

| Example | 1 | 2 |
|---|---|---|
| Aromatic | Benzene | Naphthalene |
| B-10 Oxidation @ 260° C., 40 hrs, % Visc. Increase | 81 | 14 |

We claim:

1. A process for the preparation of alkylaromatic lubricant fluids, comprising:
   alkylating at least one alkylatable aromatic compound and with an alkylating agent comprising an olefinic hydrocarbon oligomer in the presence of a solid, porous acidic alkylation catalyst comprising a crystalline material characterized by an X-ray diffraction pattern including values substantially as set out in Table 1 of the specification, to produce an alkylated aromatic hydrocarbon product.

2. A process according to claim 1 in which the synthetic porous crystalline material is characterized by an X-ray diffraction pattern including values substantially as set forth in Table 2 of the specification.

3. A process according to claim 1 in which the synthetic porous crystalline material is characterized by an X-ray diffraction pattern including values substantially as set forth in Table 3 of the specification.

4. A process according to claim 1 in which the synthetic porous crystalline material is characterized by an X-ray diffraction pattern including values substantially as set forth in Table 4 of the specification.

5. A process according to claim 1 in which the synthetic porous crystalline material has a composition comprising the molar relationship $$X_2O_3:(n)YO_2,$$

wherein n is at least about 10, X is a trivalent element and Y is a tetravalent element.

6. A process according to claim 1 in which the synthetic porous crystalline material has the structure of MCM-22.

7. A process according to claim 1 in which the alkylation is carried out under alkylation conditions comprising a temperature a temperature between −30° and 350° C., and a pressure between 700 and 7000 kPa.

8. A process according to claim 1 in which the olefin oligomer has a branch ratio greater than 0.19.

9. A process according to claim 1 in which the olefin oligomer is produced by the oligomerization of a 1-olefin having from 8 to 16 carbon atoms in the presence of a Lewis acid oligomerization catalyst.

10. A process according to claim 1 in which the olefin oligomer comprises a $C_{30}$ to $C_{50}$ liquid lubricant oligomer.

11. A process according to claim 9 in which the olefin oligomer comprises a oligomer having a viscosity of up to 1000 cs at 100° C.

12. A process according to claim 1 in which the aromatic compound comprises a monocyclic aromatic hydrocarbon.

13. A process according to claim 12 in which the aromatic hydrocarbon comprises benzene or an alkylbenzene.

14. A process according to claim 1 in which the aromatic compound comprises a bicyclic aromatic hydrocarbon.

15. A process according to claim 14 in which the aromatic hydrocarbon comprises naphthalene or a substituted naphthalene.

* * * * *